United States Patent [19]

Piotrowski et al.

[11] Patent Number: 4,875,941

[45] Date of Patent: Oct. 24, 1989

[54] DEACTIVATION OF REACTIVE ORGANOMETALLIC CONTAMINATED EQUIPMENT

[75] Inventors: Andrzej M. Piotrowski, Houston; Joseph J. Ligi, LaPorte, both of Tex.

[73] Assignee: Texas Alkyls, Inc., Deer Park, Tex.

[21] Appl. No.: 166,338

[22] Filed: Mar. 10, 1988

[51] Int. Cl.$^4$ .............................................. B08B 5/00
[52] U.S. Cl. ....................................... 134/11; 134/30; 134/31; 134/42
[58] Field of Search ...................... 134/11, 30, 31, 42

[56] References Cited

U.S. PATENT DOCUMENTS 2,248,943  7/1941  Bley ...................................... 252/302
4,617,064  10/1986  Moore ..................................... 134/11

*Primary Examiner*—Asok Pal
*Attorney, Agent, or Firm*—Richard P. Fennelly; Louis A. Morris

[57] ABSTRACT

Equipment which is contaminated with an organometallic residue is treated with gaseous carbon dioxide to react with the organometallic compounds contained in the equipment.

6 Claims, No Drawings

DEACTIVATION OF REACTIVE ORGANOMETALLIC CONTAMINATED EQUIPMENT

BACKGROUND OF THE PRESENT INVENTION

1. Field of the Invention

The present invention relates to the deactivation of reactive organometallic contaminated equipment.

2. Description of the Prior Art

When certain organometallic compounds are synthesized (e.g., certain organoaluminum or organomagnesium compounds) the equipment which is used becomes contaminated with reactive organometallic residue. It is known to use water to react with the residue, but such water deactivation is both costly and potentially hazardous due to the virorous reaction between the organometallic residue and the water which is added. Hence, a need exists for a deactivation procedure which is both less costly and hazardous than the water deactivation procedure currently used.

SUMMARY OF THE PRESENT INVENTION

The present invention relates to the deactivation of reactive organometallic-contaminated equipment by treatment of the equipment with gaseous carbon dioxide to deactivate the equipment.

DETAILED DESCRIPTION OF THE PRESENT INVENTION

The types of reactive organometallic residue which is intended to be treated in accordance with the present invention includes the organoaluminum and organomagnesium species which react vigorously with water. Included are trialkylaluminum species, such as triethylaluminum, tri-n-butylaluminum and tri-iso-butylaluminum, and dialkylaluminum hydride species, such as dibutylaluminum hydride. Others which pose a problem in regard to the deactivation of plant equipment include: alkylaluminum halides, such as diethylaluminum chloride; and alkylmagnesium species, such as butylethylmagnesium.

The equipment which can be deactivated in accordance with the present invention includes plant process vessels and other equipment associated with the manufacturing process which generates the undesired reactive organometallic residue in the equipment.

In accordance with the present invention, gaseous carbon dioxide is used to treat the contaminated equipment. The carbon dioxide acts as a mild reagent to deactivate the plant process equipment containing the organometallic contamination. The present inventors have found that the carbon dioxide reacts with the organometallic species contaminating the equipment to passivate the equipment rendering it amenable to later water washing or disassembly without the danger of either fire or explosion. Treatment with the gaseous carbon dioxide can take place over a temperature range of from about 20° C. to about 150° C. at pressures of from about 5 psi to about 100 psi. Temperatures in the neighborhood of 60° C. and pressures in the neighborhood of 25 psi have been found to give especially good results.

The foregoing invention is further illustrated by the Example which follows.

EXAMPLE 1

Triethylaluminum, TEAL, (109.4 grams) and dibutylaluminum hydride, DIBAL-H, (49.7 grams) were charged to a Fischer-Porter pressure bottle fitted with a pressure gauge, thermowell and cooling coil. The bottle was then pressurized with $CO_2$ to 10 psi. A temperature rise of 4° C. over a period of 10 minutes was observed. The pressure dropped to 4 psi over the same period. It was found that optimal conditions were approximately 60° C. and 25 psi pressure. Reaction was mild and self-controlled. A drop of pressure of $CO_2$ caused a fast drop in the reaction rate. About 1 molar equivalent of $CO_2$ was consumed over a period of 5 hours. A total of 177.0 grams of viscous product was recovered after the carbonation reaction. It was not pyrophoric on exposure to air and did not react violently with water or aqueous base.

COMPARATIVE EXAMPLE

Process vessels containing organoaluminum compounds can be opened for repairs or scheduled maintenance only after deactivation. Such deactivation is usually conducted by solvent wash followed by water wash. Solvent wash alone usually leaves substantial quantities of organometallic compounds in the vessel leading to a highly exothermic hydrolysis reaction during the water wash step. This is accompanied by generation of voluminous amounts of smoke, combustible gases and steam. In cases where water has contacted a "pocket" of unwashed organometallic residue, violent reactions have been observed.

EXAMPLE 2

A trailer (10,000-gallon capacity) filled with 2,000 lbs. of solid and liquid organometallic residue was pressurized with $CO_2$ to 24 psi over a period of five hours (185 lbs. of carbon dioxide was used). The vessel was left under pressure for a period of 24 hours and then vented, purged with nitrogen, and opened to the atmosphere. No smoke was observed which was in great contrast to previous cases where such vessels were not treated with $CO_2$ (a voluminous amount of smoke was usually observed when the contents of the vessel were exposed to air). The trailer was then filled with water. No smoke or steam was evolved.

EXAMPLE 3

A process vessel (1,800-gallon capacity) containing triethylaluminum residue was pressurized with $CO_2$ to 30 psi over a period of three hours (85 lbs. of carbon dioxide was used). The temperature in the vessel rose from 85° F. to 102° F. After 12 hours, the vessel was vented, purged with nitrogen, and opened to the atmosphere. Very little smoke evolution was observed, and it quickly subsided. The vessel was then slowly filled with water. There was no generation of steam or smoke. When the same vessel was only solvent-washed, prolonged evolution of dense smoke, combustible gases and steam was observed.

The foregoing Examples are presented for illustrative reasons only and should not be construed in a limiting sense. The scope of protection that is sought is set forth in the claims which follows.

We claim:

1. A method for the treatment of organometallic-contaminated equipment which comprises treating the equipment with gaseous carbon dioxide so as to react with organometallic compounds contaminating the equipment.

2. A method as claimed in claim 1 wherein the treatment with gaseous carbon dioxide takes place at from about 20° C. to about 150° C.

3. A method as claimed in claim 1 wherein the treatment with gaseous carbon dioxide takes place at pressures of from about 5 psi to about 100 psi.

4. A method as claimed in claim 1 wherein the treatment with gaseous carbon dioxide takes place at from about 20° C. to about 150° C. and at pressures of from about 5 psi to about 100 psi.

5. A method as claimed in claim 1 wherein the organometallic compounds are selected from the group consisting of organoaluminum compounds and organomagnesium compounds.

6. A method as claimed in claim 4 wherein the organometallic compounds are selected from the group consisting of organoaluminum compounds and organomagnesium compounds.

* * * * *